(12) United States Patent
Cobb et al.

(10) Patent No.: US 10,347,363 B2
(45) Date of Patent: Jul. 9, 2019

(54) OPTICAL PROCESSING

(71) Applicant: Genedrive Diagnostics Ltd, Manchester (GB)

(72) Inventors: Benjamin David Cobb, Wiltshire (GB); David Andrew Barr, Lisburn (GB)

(73) Assignee: Genedrive Diagnostics Ltd, Manchester (GB)

( * ) Notice: Subject to any disclaimer, the term of this patent is extended or adjusted under 35 U.S.C. 154(b) by 0 days.

(21) Appl. No.: 16/002,827

(22) Filed: Jun. 7, 2018

(65) Prior Publication Data

US 2018/0300452 A1 Oct. 18, 2018

Related U.S. Application Data (62) Division of application No. 14/431,914, filed as application No. PCT/GB2013/052104 on Aug. 7, 2013, now Pat. No. 10,019,550.

(30) Foreign Application Priority Data

Sep. 27, 2012 (GB) .................................. 1217242.5

(51) Int. Cl.
| | | |
|---|---|---|
| C12Q 1/686 | (2018.01) | |
| G16B 30/00 | (2019.01) | |
| G16B 40/00 | (2019.01) | |
| G01N 21/64 | (2006.01) | |
| B01L 7/00 | (2006.01) | |

(52) U.S. Cl.
CPC .............. *G16B 30/00* (2019.02); *B01L 7/52* (2013.01); *C12Q 1/686* (2013.01); *G01N 21/64* (2013.01); *G01N 21/6428* (2013.01); *G01N 21/6486* (2013.01); *G16B 40/00* (2019.02)

(58) Field of Classification Search
CPC .............. C12Q 1/686; C12Q 2527/107; C12Q 2537/165; C12Q 2561/113; B01L 7/52; G01N 21/64; G01N 21/6428; G01N 21/6486; G06F 19/22; G06F 19/24
USPC ............................................. 435/283.1, 91.2
See application file for complete search history.

(56) References Cited

U.S. PATENT DOCUMENTS

| | | | |
|---|---|---|---|
| 6,121,053 | A | 9/2000 | Kolber et al. |
| 6,472,156 | B1 | 10/2002 | Wittwer et al. |
| 10,019,550 | B2 | 7/2018 | Cobb et al. |
| 2003/0104438 | A1 | 6/2003 | Eyre et al. |
| 2004/0014119 | A1 | 1/2004 | Itoh et al. |
| 2004/0066551 | A1* | 4/2004 | Lelic .................. H01S 3/06754 359/341.41 |
| 2004/0222384 | A1 | 11/2004 | Lee et al. |
| 2005/0233335 | A1 | 10/2005 | Wittwer et al. |
| 2008/0201103 | A1 | 8/2008 | Yang et al. |
| 2009/0112481 | A1 | 4/2009 | Cao |
| 2009/0222503 | A1 | 9/2009 | Palais et al. |
| 2010/0285571 | A1 | 11/2010 | Coursey et al. |
| 2011/0010103 | A1 | 1/2011 | Kanderian |
| 2011/0111968 | A1* | 5/2011 | Okura ...................... B01L 7/00 506/7 |
| 2011/0231132 | A1 | 9/2011 | Gunstream |
| 2011/0238323 | A1* | 9/2011 | Robbins ................. G06F 19/20 702/19 |
| 2011/0250649 | A1 | 10/2011 | Li et al. |
| 2015/0248524 | A1 | 9/2015 | Cobb et al. |

FOREIGN PATENT DOCUMENTS

| | | |
|---|---|---|
| EP | 1880175 A2 | 1/2008 |
| EP | 2021773 A1 | 2/2009 |
| WO | WO-00/66777 A2 | 11/2000 |
| WO | WO-2006/119277 A2 | 11/2006 |
| WO | WO-2007/119067 A1 | 10/2007 |
| WO | WO-2012/054028 A1 | 4/2012 |

OTHER PUBLICATIONS

El-Hajj, H. et al., Use of Sloppy Molecular Beacon Probes for Identification of Mycobacterial Species, Journal of Clinical Microbiology, 47(4):1190-1198 (2009).
International Search Report for PCT/GB2013/052104, 5 pages (dated Mar. 5, 2014).
Monteiro, J. et al., Rapid detection of carbapenemase genes by multiplex real-time PCR, J. Antimicrob Chemother, 67:906-909 (2012).
Search Report for GB1217242.5, 4 pages (dated Dec. 7, 2012).

* cited by examiner

*Primary Examiner* — Cynthia B Wilder
(74) *Attorney, Agent, or Firm* — Choate, Hall & Stewart LLP; Brenda Herschbach Jarrell; Michael L. Vetter (57) ABSTRACT

We describe a quantitative PCR (qPCR) instrument for combined qPCR and melt curve (dissociation and/or association curve) analysis. The instrument has at least one optical channel; a fluorescence excitation source; a fluorescence detector; an electronic analog signal amplifier having an input coupled to an output of the fluorescence detector; and an analog-to-digital converter (ADC) having analog input coupled to an output of the analog signal amplifier. The instrument further comprises a quantified automatic gain control (AGC) loop coupled between the signal output of the fluorescence detector and the analog input of the ADC. The AGC loop is configured to apply a determined, numerical gain value to a fluorescence signal for the analog input of the ADC. The instrument also includes a system to scale a digital output of the ADC responsive to the numerical gain value and to provide a digital fluorescence level signal from the scaled digital output.

9 Claims, 11 Drawing Sheets

OPTICAL PROCESSING

CROSS REFERENCE TO RELATED APPLICATIONS

The present application is a divisional application of U.S. application Ser. No. 14/431,914, filed Mar. 27, 2015, which is a U.S. National Phase Application filed under 35 U.S.C. § 371 based on International Application PCT/GB2013/052104, filed Aug. 7, 2013 and published as WO 2014/049323 on Apr. 3, 2014, which claims priority to United Kingdom patent application serial number GB 1217242.5 filed Sep. 27, 2012, the entire contents of which are incorporated herein by reference.

FIELD OF THE INVENTION

The invention relates to qPCR (quantitative polymerase chain reaction) instruments, and to related methods, apparatus and software for analysing fluorescence data from a dissociation and/or association curve such as a melt curve, for example of a PCR product.

BACKGROUND TO THE INVENTION

As double stranded DNA (dsDNA) is heated it dissociates or melts, that is the two strands separate. The melting temperature may, for example, be in the range 60-90° C. The melting temperature (Tm) depends upon a range of factors including, by way of example, GC-content (guanine-cytosine content), the length of the DNA strand (or amplicon length), the degree of methylation, and secondary and tertiary structure. Further, where there is a mismatch between a probe and a target sequence, for example due to the presence of a SNP (single nucleotide polymorphism) then the melting temperature will differ compared with when there is no mismatch. Thus, for example, it can be useful to detect changes in melting temperature of DNA-hybridisation between a specific oligonucleotide probe and a gene target when a SNP is present. Melting point analysis is often used in conjunction with PCR (polymerase chain reaction) amplification, for example to amplify somatic cell mutations which may only be present in a very few copies in a sample. More particularly in real time quantitative PCR (qPCR) melt/dissociation curve analysis can be used to determine the number and/or approximate size of PCR products. Thus a melt curve may have one or more peaks depending upon the product or products present (the identities of products may be determined by fractionating the product(s) on a gel). According to one definition the melting temperature, Tm, may be defined as the temperature at which 50% of the DNA sample is double stranded and 50% of the sample is single stranded.

Typically a melt curve is determined by measuring the change in fluorescence of a double stranded DNA sample with temperature, more particularly by observing the reduction in fluorescence due to melting of the dsDNA. In one approach a DNA-binding dye is employed. Typically such a dye is non-specific and binds to dsDNA, for example generated during PCR amplification; the dye is highly fluorescent when bound to dsDNA but exhibits only a low fluorescence when not bound. Thus there is a reduction in fluorescence when the dsDNA melts. Such dyes typically operate by intercalation and/or minor groove binding; examples are SYBR™ Green and quencher-labelled primers. Alternatively sequence specific fluorescent DNA-based probes may be employed, typically containing a fluorescent element and a quenching element such that when the probe hybridises to the complementary target these elements are separated so that a fluorescent signal is generated.

Figure 1A:
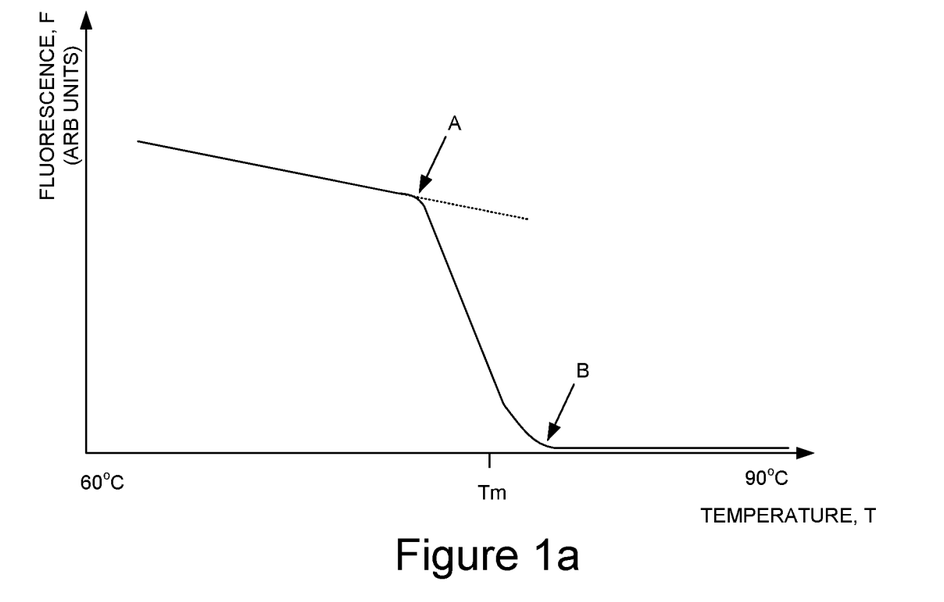
FIGS. 1a and 1b show, respectively, raw and derivative data for a typical fluorescence melt curve.
Figure 1B:
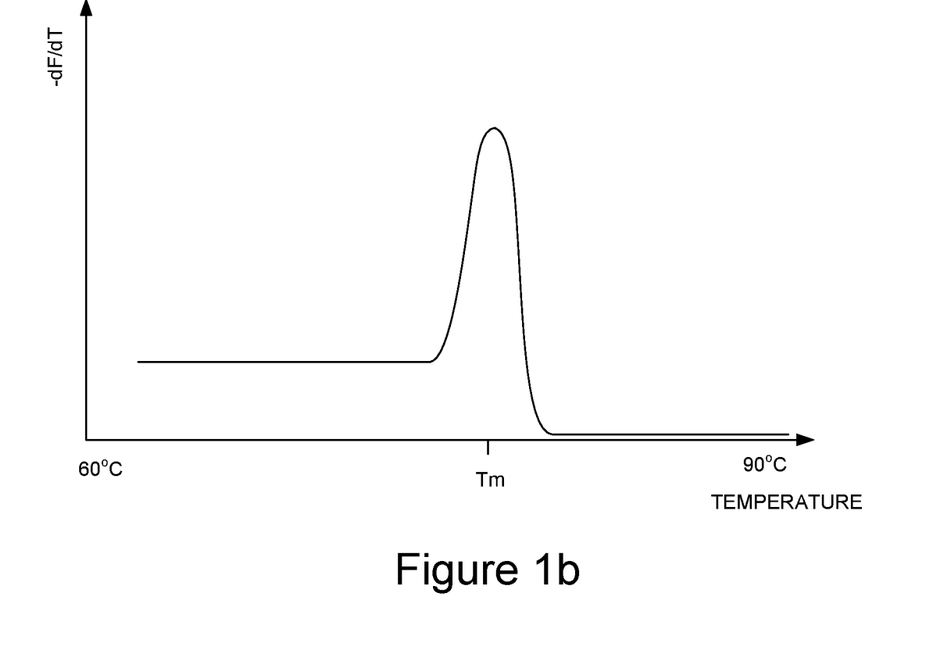

FIG. 1a shows, schematically, a typical fluorescence melt curve with fluorescence (in arbitrary units) on the Y axis and temperature on the X axis. Initially the fluorescence exhibits a linear decrease with increasing temperature until a point A is reached at which the fluorescence drops below the level predicted by this linear decrease as the dsDNA begins to melt. Eventually, at point B, the melting is complete and the fluorescence level drops towards zero. A melt curve is often plotted as the negative first derivative of the fluorescence signal with respect to temperature ($-dF/dT$) as shown schematically in FIG. 1b. This facilitates determine the melting temperature, which correspondents to the peak of the derivative curve (the maximum slope of the fluorescence curve).

Although melt/dissociation curve analysis is typically performed by determining the derivative of the fluorescence signal with temperature this is not essential. For example in some other approaches melt curve analysis is performed directly on the fluorescence signal, which is typically then normalised amongst samples for comparison.

Figure 2A:
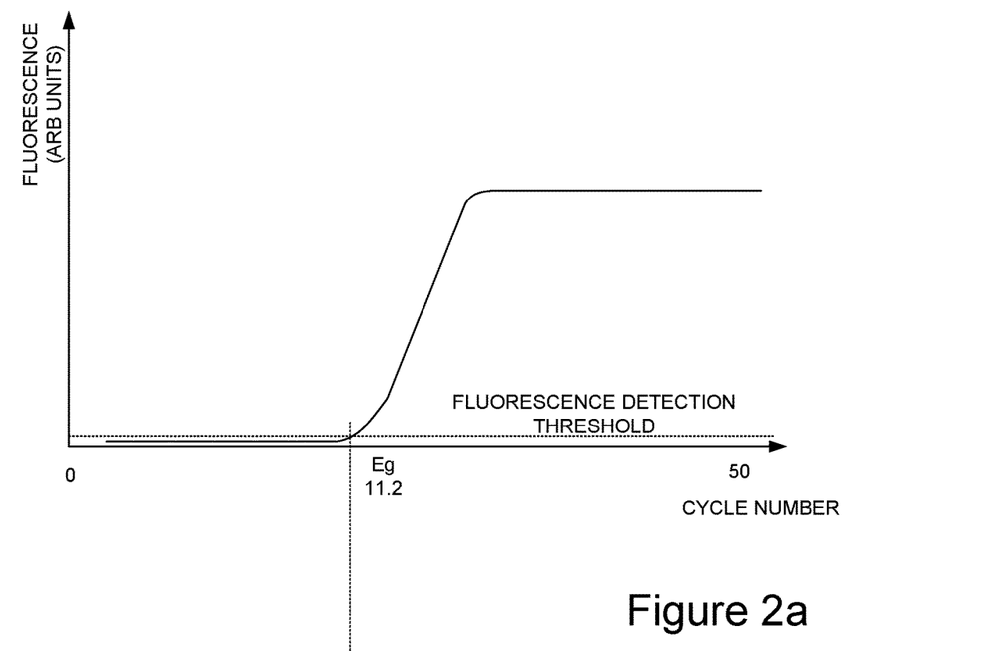
FIGS. 2a and 2b show, respectively, linear and semi-log plots of fluorescence against cycle number for a typical qPCR experiment, illustrating the cycle threshold.
Figure 2B:
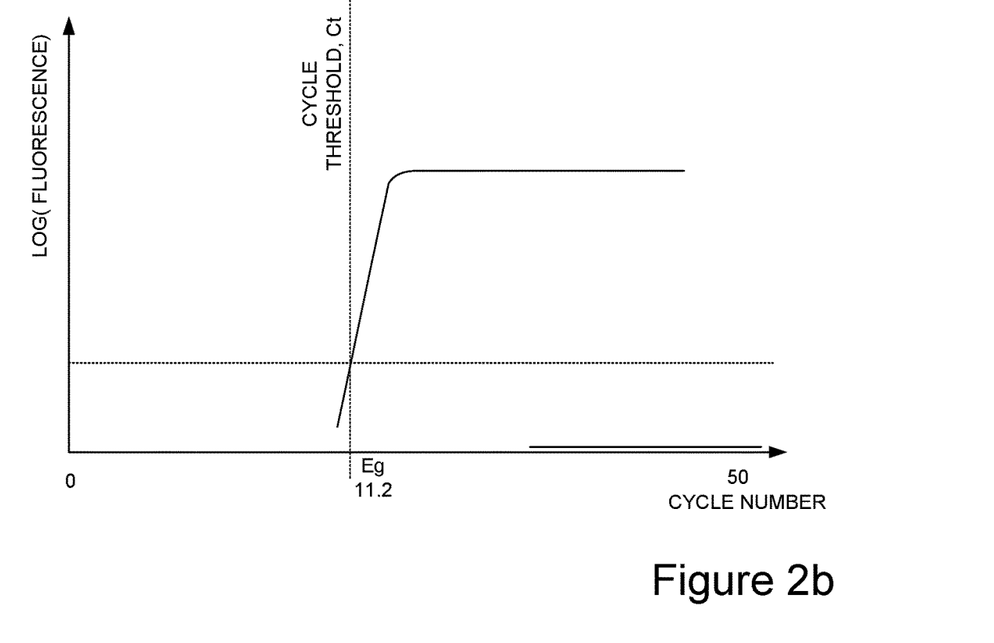

As shown in FIG. 2, in quantitative PCR there is phase during which the amount of target grows exponentially prior to some limiting point (linear on a semi-log plot). The amount of DNA initially present in a sample can be determined from the point at which fluorescence is first detected above the background level—this is referred to as the cycle number threshold (Ct) or crossing point. This is inversely correlated to the logarithm of the initial copy number. Initially the level of fluorescence from the amplified PCR product is too low to be detected but after a number of PCR cycles, depending upon the initial amount of sample DNA, the product is detectable. The sooner the accumulated product is detected, the lower the cycle number threshold, and the higher the initial amount of sample DNA. For accuracy, and to detect lower levels of sample DNA, it is desirable for the instrument to detect low levels of fluorescence signal (although the background level can drift).

Particularly in an instrument which is able to perform melt curve analysis, the desire for high sensitivity conflicts with the need to obtain accurate melt temperatures, which can be affected by saturation/limiting of the fluorescence detection at high signal levels.

We will describe techniques which address these and other problems associated with PCR, in particular qPCR, and melt/dissociation curve analysis.

SUMMARY OF THE INVENTION

According to the invention there is therefore provided a quantitative PCR (qPCR) instrument for combined qPCR and dissociation and/or association curve analysis, the instrument having at least one optical channel, the instrument comprising: a fluorescence excitation source; a fluorescence detector having a signal output; an electronic analogue signal amplifier having an input coupled to said fluorescence detector signal output; and an analogue-to-digital converter (ADC) having analogue input coupled to an output of said analogue signal amplifier; further comprising a quantified automatic gain control (AGC) loop coupled between said signal output of said fluorescence detector and said analogue input of ADC, wherein said AGC loop is configured to apply a determined, numerical gain value to a fluorescence signal for said analogue input of said ADC; and a system to scale a digital output of said ADC responsive to said numerical gain value and to provide a digital fluorescence level signal from said scaled digital output.

Embodiments of the instrument provide a continuum of response substantially without the discontinuities which might otherwise be expected to be observed with changes in photogain. The technique is also suitable for rapid data acquisition, for example, one sample every 100 ms or faster. The digital fluorescence level signal may be provided as an output from the instrument and/or may be used internally, for example to determine a Ct value for a qPCR run. In embodiments the dissociation/association curve is a melt curve.

Preferred embodiments of the instrument employ a digitally controllable analogue electronic gain control circuit (here gain optionally including attenuation) and a digital signal processing system coupled to the output of the ADC. The digital signal processing system may be, for example, a general purpose computer running appropriate software, or a microcontroller, or a DSP (digital signal processing) integrated circuit and/or may be partially implemented in dedicated hardware. The digital signal processing system is configured to determine the numerical gain value for the gain control loop, and to apply this known gain in the analogue signal domain, then scaling the ADC output in the digital domain to compensate. The known gain provided by the analogue electronic gain control circuit may be known by design, for example appropriate choice of component values, or from calibration, or both.

Preferably the qPCR instrument includes a calibration system comprising means for controlling the gain of the analogue signal path, and software running on the digital signal processing system, to determine and store an initial calibration value of the electronic gain of this path in non-volatile memory. In a multi-channel instrument the digital signalling processing system is preferably also configured to scale or normalise the channels so that the digital outputs from each match when the same fluorescent light signal is incident upon the fluorescence detector of the respective channel. Preferably the channel with the largest ADC digital output is selected to scale to (for maximum sensitivity) and the other digital outputs are scaled up to match this.

In this manner a 'factory gain' can be determined for the or each channel. This is afterwards automatically applied to all fluorescence level signals in the digital domain to convert the digital ADC output into a standard, albeit potentially arbitrary, fluorescence level signal. Then when the AGC loop during operation applies an additional run time gain $R_G$ multiplying, say, a very small fluorescence signal into a larger analogue level prior to ADC conversion, the digital ADC value may then be scaled down (dividing by $R_G$), to thereby measure a potentially very low fluorescence signal with high accuracy.

In preferred embodiments one or preferably both of the AGC control loop and initial calibration include a system for inhibiting saturation of the ADC. Thus, for example, at initial calibration the analogue signal amplifier gain may be increased so that the ADC digital output is just below a maximum available digital output from the ADC, for example greater than a lower threshold (so that the output is close to the maximum) but below an upper threshold (so that the signal does not quite reach the maximum, saturation value).

In preferred implementations the AGC control loop is implemented in software with a loop response time (to determine a new AGC value) of less than 500, 200, 100 or 50 ms.

In a related aspect the invention provides a method of operating a qPCR instrument, the instrument including: a fluorescence excitation source; a fluorescence detector having a signal output; an electronic analogue signal amplifier having an input coupled to said fluorescence detector signal output; and an analogue-to-digital converter (ADC) having analogue input coupled to an output of said analogue signal amplifier; the method comprising: calibrating said optical channel by adjusting an electronic gain of said electronic analogue signal amplifier; storing a calibration value of said electronic gain in non-volatile memory; applying automatic gain control (AGC) to an analogue electronic signal path of said optical channel during qPCR, wherein said AGC includes digitally determining a numerical gain value for said AGC; and determining a digital fluorescence level signal by scaling a digitised fluorescence signal from said optical channel by both said calibration value of said electronic gain and said determined numerical gain value for said AGC.

It is particularly advantageous to continue to use the instrument after a qPCR experiment or diagnostic run to perform one or measurements on a result of the qPCR experiment/run, continuing to apply the AGC in the same manner as previously. This allows, for example, melt curve analysis to compare melting temperatures of amplification products.

The above described instruments are useful for a range of qPCR techniques including, in particular, absolute quantitation, relative quantitation, and qualitative analysis. The techniques may be applied to DNA and/or RNA (for example in qRT-PCR-quantitative reverse transcription PCR).

In a related aspect the invention provides a quantitative PCR (qPCR) instrument for combined qPCR and dissociation and/or association curve analysis, the instrument having at least one optical channel, the instrument comprising: a fluorescence excitation source; a fluorescence detector having a signal output; an electronic analogue signal amplifier having an input coupled to said fluorescence detector signal output; an analogue-to-digital converter (ADC) having analogue input coupled to an output of said analogue signal amplifier; means for calibrating said optical channel by adjusting an electronic gain of said electronic analogue signal amplifier; means for storing a calibration value of said electronic gain in non-volatile memory; means for applying automatic gain control (AGC) to an analogue electronic signal path of said optical channel during qPCR, wherein said AGC includes digitally determining a numerical gain value for said AGC; and means for determining a digital fluorescence level signal by scaling a digitised fluorescence signal from said optical channel by both said calibration value of said electronic gain and said determined numerical gain value for said AGC.

In some preferred implementations the instrument has multiple optical channels for processing multiple samples simultaneously, for example for quantifying a library by qPCR.

As the skilled person will appreciate, the fluorescence excitation source may comprise one or more of a tungsten lamp, laser or LED (light emitting diode). Optionally appropriately filtered; the detector may comprise, for example, a photomultiplier tube, photodiode or CCD (charged couple device) array. Optionally in embodiments the digital signal processing system may automatically perform a qPCR and/or end point analysis experiment, for example outputting one or more Ct values and/or melting temperature values.

Additionally or alternatively raw or processed data and/or a graphical output may be provided.

We will also describe some improved techniques for melt/dissociation curve analysis. These techniques may advantageously be employed with the above described qPCR instrument, but they may also be used independently.

Thus according to another aspect of the invention there is therefore provided a method of processing dissociation and/or association curve data, the method comprising: inputting fluorescence data representing fluorescence (F) for a temperature (T) range including a double stranded DNA melting temperature; determining fluorescence derivative data representing a derivative (dF/dT) of said fluorescence with temperature; identifying a largest peak of said fluorescence derivative data; scaling said fluorescence derivative data such that said largest peak has a maximum at a defined value to provide scaled fluorescence derivative data; determining a cumulative measure of said scaled fluorescence derivative data over said temperature range; repeating said identifying, scaling and determining of said cumulative measure for successively small peaks of said fluorescence data until cumulative measure is greater than a threshold value; and outputting data representing temperatures of said identified peaks.

Embodiments of this method facilitate identifying genuine, significant peaks within what can often be an imperfect fluorescence signal. The cumulative measure determined from the scaled fluorescence derivative data may, for example, be an average, an integral under the curve of the scaled fluorescence derivative data, or some other measure. In embodiments, therefore, the procedure iteratively, or recursively, identifies successively smaller peaks of the fluorescence derivative data by, in effect, normalising successively smaller peaks until a magnification limit is reached.

Thus in a related aspect the invention provides a method of processing dissociation and/or association curve data, the method comprising: inputting fluorescence data representing fluorescence (F) for a temperature (T) range including a double stranded DNA melting temperature; determining fluorescence derivative data representing a derivative (dF/dT) of said fluorescence with temperature; and identifying successively smaller peaks in said fluorescence derivative data by magnifying said fluorescence derivative data to normalise successively smaller peaks until a magnification limit is reached.

In preferred embodiments of the technique the fluorescence derivative data is processed so that one or more minima of the processed fluorescence derivative data lies substantially at a zero level. In this way at least the next smallest peak begins at a zero level prior to scaling to provide the standardised/normalised waveform, and then averaging to determine the cumulative measure.

Preferably the fluorescence derivative data is processed prior to identifying the largest and successively smaller peaks so that this data defines values at or above zero (or at least not substantially less than zero) over a majority, preferably substantially all of the temperature range. In embodiments at least the largest peak is bounded by minima at or above zero. In one preferred implementation this is achieved by subtracting an offset and adjusting the fluorescence derivative data to smoothly tend towards zero towards start and end points at respective ends of the temperature range. This may be achieved by subtracting one or more straight line functions from the fluorescence derivative data, where a straight line function defines a linear change of fluorescence derivative values with temperature. In some approaches a piecewise linear function is subtracted from the fluorescence derivative data, the piecewise linear function joining end points and any minima of the waveform.

In embodiments the determining of the fluorescence derivative data includes smoothing this data over a window of fluorescence sample values, in effect low-pass filtering this data. Optionally one or more additional smoothing/low-pass filtering may be performed during the procedure for identifying the successively smaller peaks. In one implementation two sets of peaks are identified, one employing less smoothing/low-pass filtering of the fluorescence derivative data than the other. The derivative data with less filtering exhibits many more peaks and, preferably, false positives are filtered out by rejecting peaks in this set which lie beyond the threshold distance from a peak in the more heavily filtered set. The threshold distance may be determined by the noise level in the fluorescence data/fluorescence derivative data. For example in embodiments this threshold distance may be 4, 3, 2 or 1 standard deviations of the data from a peak in the more heavily filtered data.

The invention also provides dissociation and/or association curve analysis apparatus, the apparatus comprising: an input to receive fluorescence data representing fluorescence for a temperature range including a double stranded DNA melting temperature; an output to provide temperature data; and a processor, coupled to said input, to said output, to working memory and to program memory, said program memory storing instructions for controlling the processor to: determine fluorescence derivative data representing a derivative (dF/dT) of said fluorescence with temperature; identify a largest peak of said fluorescence derivative data; scale said fluorescence derivative data such that said largest peak has a maximum at a defined value to provide scaled fluorescence derivative data; determine a cumulative measure of said scaled fluorescence derivative data over said temperature range; repeat said identifying, scaling and determining of said cumulative measure for successively small peaks of said fluorescence data until cumulative measure is greater than a threshold value; and output data representing temperatures of said identified peaks.

The invention further provides processor control code to implement the above-described systems and methods, for example on a general purpose computer system or on a digital signal processor (DSP). The code is provided on a physical data carrier such as a disk, CD- or DVD-ROM, programmed memory such as non-volatile memory (e.g. Flash) or read-only memory (Firmware). Code (and/or data) to implement embodiments of the invention may comprise source, object or executable code in a conventional programming language (interpreted or compiled) such as C, or assembly code. As the skilled person will appreciate such code and/or data may be distributed between a plurality of coupled components in communication with one another.

In some preferred implementations the above described techniques for processing dissociation and/or association curve data are incorporated into a (q)PCR instrument of the type previously described.

BRIEF DESCRIPTION OF THE DRAWINGS

These and other aspects of the invention will now be further described by way of example only, with reference to the accompanying figures in which.

DETAILED DESCRIPTION OF PREFERRED EMBODIMENTS

As previously described, one of the challenges in the measurement of fluorescence during real time PCR is maximising the signal to noise ratio (SNR) with any given reporter fluorophore whilst preventing the overall saturation of the optical system with the signal generated by the fluorophore. This is often confounded by the fact that there are often large differences in fluorescence outputs between different fluorophores and even between probes with different sequences that use the same fluorophore. Probes that generate smaller fluorescence signals require higher gain settings to those that produce high signals.

This is particularly problematic for end-point measurements such as melt curve measurements, where a saturated signal will affect the melt curve response and the accuracy of determining the absolute position of the melt peak if the point at which the fluorescence signal diminishes is above the saturation threshold. This tends to shift the position of the peak to the right hand side providing higher apparent melting temperatures than the true or predicted temperature. During melt curve analysis it is generally important to keep the gain within a range that maximises the fluorescence response at points between the maximum and minimum fluorescence. This can be achieved by using a fixed amplifier gain setting that is set at the start of the melt process or that is fixed during the entire analysis process. The gain setting is selected to be low enough so that the optical measurement does not become saturated at the high fluorescence extreme and can therefore capture the entire fluorescence range during the melt analysis.

It is relatively straightforward in this scenario since the instrument can measure the maximum fluorescence at the end of the PCR in the knowledge that the fluorescence has peaked and reached its maximum. However, with some probe chemistries, there may be an increase in signal prior to the decay during the melt and it becomes a compromise between establishing a gain setting that can capture the entire extremities of the melt curve fluorescence response curve.

With real time PCR it is more difficult to predict where the fluorescence signal is likely to end up at the end of the process. Here, it is preferable to keep the gain as high as possible in order to be able to accurately measure the cycle threshold at the earliest point; cycle threshold is the first point in the cycle at which product accumulation can be confidently observed as an increase in fluorescence. Since the instrument cannot predict where the fluorescence signal will end up, the photogain is set within a window that is not too high to risk saturation, and not too low to limit the sensitivity of measurement. These two requirements are opposed and it is often the case that the system is set up where the gain is set correctly for either end-point measurement or real time measurement but is sub-optimum for both.

An instrument may rely on initial settings to be set for photogains that are based on this compromise. This can be acceptable for research instruments where the operator can adjust the gain settings at the start of the process and repeat the experiment with different settings if they are shown to be suboptimal for the data acquisition required for the analysis. However this is not appropriate for diagnostic instruments where the operator cannot repeat the test. This is even more acute for diagnostic instruments where a number of different tests running different probe chemistries may be required to run on the same platform.

Thus we describe techniques which allow an instrument to continually adjust its photogain settings such that the system is always close to the maximum photogain response possible and avoids becoming saturated either during the PCR or during end-point analysis. This results in a system that is in a maximum response window for both real time measurement and melt-curve measurement, regardless of the chemistry being used. The described system also provides a unit in which each channel can have a different photogain setting within the optimum response window; channels are mathematically adjusted so that they are appropriately scaled to be on the same overall scale. The response scale effectively becomes a continuum where the different photogain settings are mathematically adjusted over a much larger dynamic range without user intervention. Even with fast/frequent data acquisition (for example once every 100 ms), a continuum of response is provided, without discontinuities in the measurement with each change in photogain that would otherwise need to be accommodated for in the signal processing.

Figure 3:
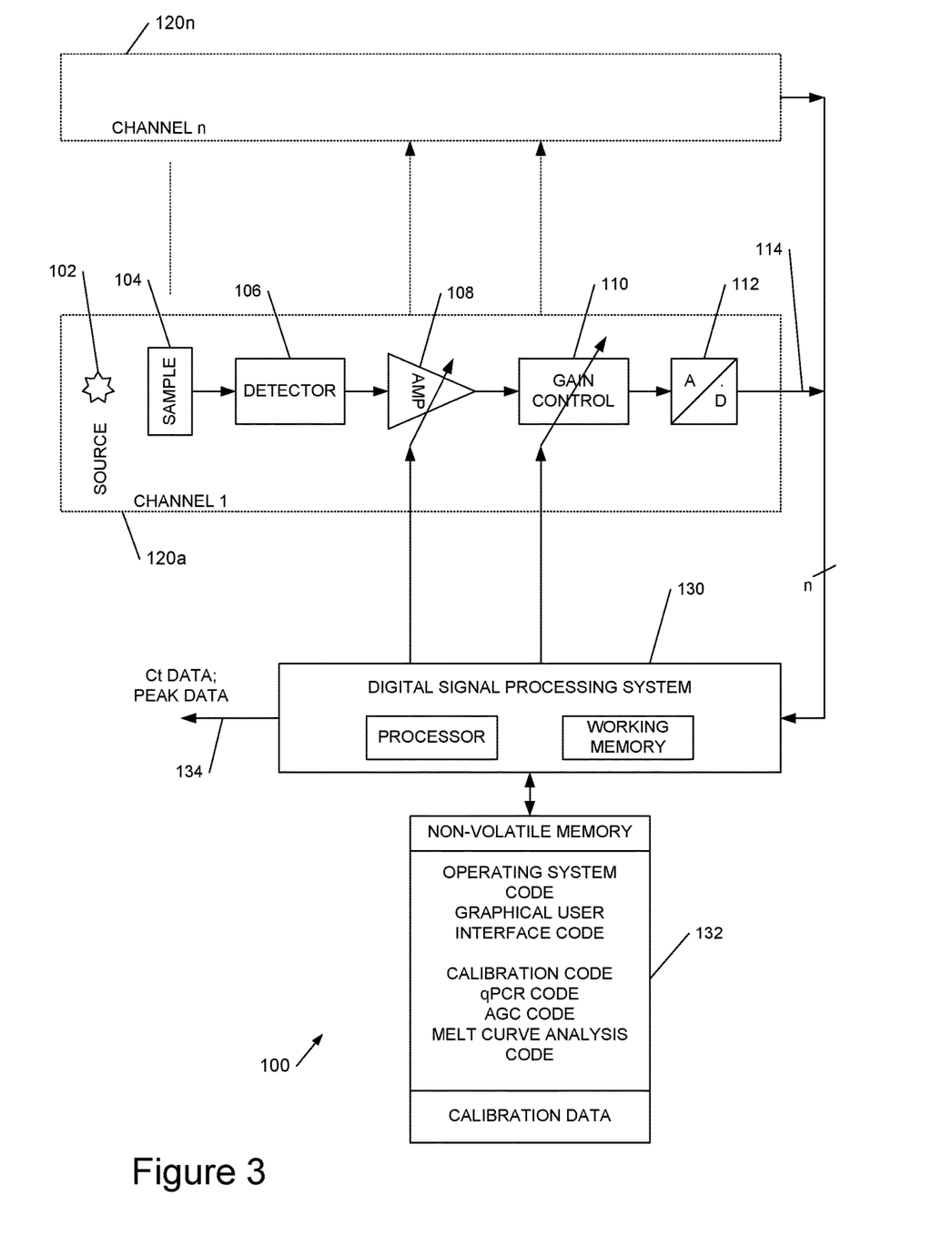
FIG. 3 shows a schematic block diagram of a qPCR instrument according to an embodiment of the invention.

Thus referring to FIG. 3, this shows a simplified schematic block diagram of a multichannel qPCR instrument 100 configured to implement the techniques we describe. The instrument has n channels 120a-n, each comprising a fluorescence excitation light source 102, for example an LED, arranged to illuminate a sample 104, the fluorescence from which is detected by a detector 106, for example a photomultiplier tube in conjunction with one or more filters. This provides a signal to an electronic amplifier 108 and to a variable electronic gain control unit 110 (in embodiments these may be combined). These in turn provide a signal to an analogue input of an analogue-to-digital converter 112 which provides a digitised signal output 114, which is provided to a digital signal processing system 130. Optionally ADC 112 may be shared between multiple channels.

The digital signal processing system 130 is coupled to non-volatile memory 132 storing operating software and data for the instrument, in embodiments: operating system code, graphical user interface code, calibration code, qPCR control code (for general purpose control/operation of the instrument), AGC (automatic gain control) code and melt curve analysis code, as well as calibration data. The stored code operates as described later to provide output data on interface 134 for identifying a Ct (cycle threshold) value, and for identifying a dsDNA melting temperature (Tm), preferably for multiple peaks, preferably within a tolerance of 0.1° C. or better.

The calibration code is configured to implement an optical calibration procedure as follows:
Optical Calibration for a Three Channel Example a. Insert identical fluorescing tubes in all 3 channels—the purpose of calibration is to determine the differences between optical paths. Set the temperature at 50° C.
b. Pulse the LED (at max) in each channel for 250 ms each, sample the fluorescence during that 250 ms once every 1 ms, find the average sample value from those samples between 80 ms and 200 ms during that 250 ms window and report that average sample value from each of the 3 channels
c. If the ADC value in a given channel is less than 3200 then step up the amplifier 108 gain in that channel and repeat from step (b)
d. If the ADC value in a given channel is greater than 3500 then step down the amplifier 108 gain in that channel and repeat from step (b)
e. Each time the step direction changes, divide the step size by 2. When the step size becomes smaller than, say, 1 then stop adjusting at step (c) and step (d)
f. As a result a value of gain will be arrived at for each channel that will maximise the ADC value in each channel
g. Find the scaling factor S1 necessary by which to multiply the second largest ADC value in order to make it equal to the largest ADC value
h. Find the scaling factor S2 necessary by which to multiply the third largest ADC value in order to make it equal to the largest ADC value
i. As a consequence, obtain the three overall gain values (electronic gain multiplied by scaling factor) G1, G2, G3 for the three channels and thereafter maintain these overall gain values constant on all future fluorescence measurements.
j. Save these values G1, G2 and G3 in EPROM.

Broadly speaking, a result of this calibration procedure is to ensure that each channel provides the same (processed) digital output for the same input fluorescence signal at the optical detector. The digital output for the calibration samples is in the range 3200 to 3500 (the upper limit being chosen so that the ADC does not saturate).

The Gi values determine a "factory gain" $F_G$ for each channel—i.e. the digital ADC output from a channel, multiplied by $F_G$, provides a value for the detected fluorescence level (in arbitrary units or, optionally, calibrated).

During run-time operation of the instrument an automatic gain control procedure is operated which aims to maximise the electronic (analogue) gain without saturating the ADC. Thus the AGC code is configured to implement a gain control procedure as explained below.

Run-Time Automatic Gain Adjustment

In one embodiment the run-time automatic gain adjustment implements a procedure corresponding to steps (b) to (f) above, thereby achieving a high level of electronic gain without causing saturation of the ADC value. This process achieves a value of electronic gain, the run time gain ($R_G$) for each channel. (This is likely to be different for each channel due to minor differences in optical path). The run time gain is then used in conjunction with the stored factory calibration gain $F_G$ for each individual channel in order to obtain a run-time value for a scaling factor $S_F$. This is applied to the raw ADC values to calculate a final output fluorescence based on:

$$S_F = F_G/R_G$$

Thereafter, all raw ADC values (obtained as per step 1b above) are multiplied by the scaling factor $S_F$ for each individual channel to calculate the output fluorescence.

For example, if the electronic run time gain $R_G$ applied on the analogue side of the ADC is, say, ×1000, then the calculated fluorescence (given by the digital ADC value multiplied by the factory gain $F_G$) is divided by $R_G$ (i.e. 1000) on the digital side. Thus the digital ADC value is scaled by $S_F = F_G/R_G$ to obtain a fluorescence signal level which is consistent with, and effectively on the same continuous scale as, the fluorescence values determined by the initial calibration.

The skilled person will appreciate that as a consequence, if very low fluorescing material is used for the initial calibration then steps (c) and (d) above will force the electronic gain and therefore the overall gain to a very high level. This means that when highly fluorescing material is tested, because this high overall gain value is maintained, then the output fluorescence values are consequently also very high.

Saturation Prevention

If at any time during run-time a value of raw ADC is obtained that is greater than 3500, then the gain setting in that specific channel is reduced by 10 steps, resulting in a new value of $R_G$ and an amended value for $S_F$. The resulting output fluorescence waveform shows no flattening as a result of saturation and also shows no discontinuity as a result of gain adjustment.

Figure 4:
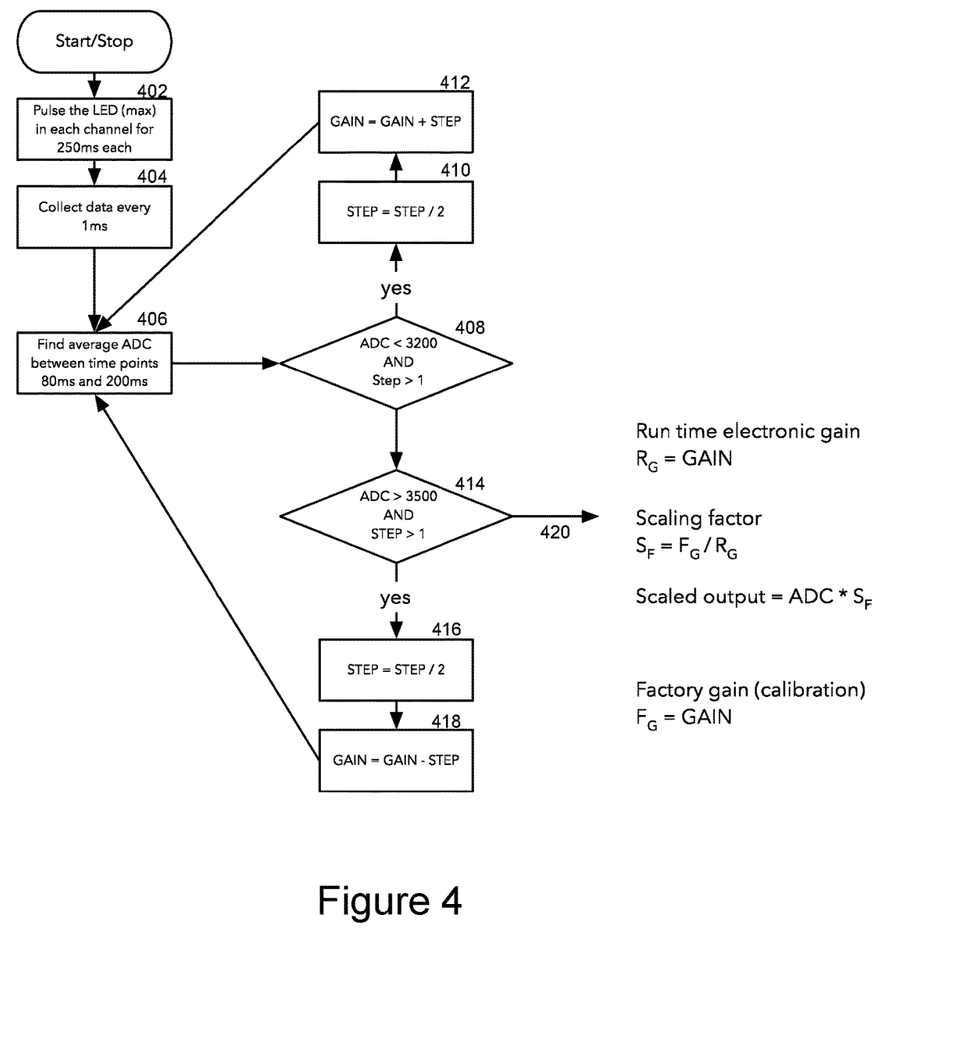
FIG. 4 shows a flow-diagram of a photogain adjustment procedure for the instrument of FIG. 3, for providing the instrument with a continuous gain response.

Referring now to FIG. 4, this shows a flow-diagram of software implementing an embodiment of a photogain adjustment procedure for the instrument of FIG. 3, as described above.

Thus when the procedure starts it pulses the LED in each channel (step 402) preferably at a maximum level, for a predetermined interval for example 250 ms each channel. During this process the system captures data every 1 ms (step 404) and then determines the average ADC value over a period within the data capture window, for example between time points 80 ms and 200 ms (step 406). The procedure then determines whether the ADC digital output is less than the lower threshold, for example 3200, and whether, at the same time, the step size is still greater than a predetermined minimum, for example unity (step 408). If this is true the procedure halves the step size (step 410) and increments the gain by the step (step 412) then repeating the measurement (step 406). If the ADC value is not less than the minimum threshold then the procedure checks whether the digital ADC output is greater than the upper threshold, for example 3500 and whether at the same time the step size is greater than unity (step 414). If this is true the step size is halved (step 416) and the gain decremented by the step value (step 418) before the measurement is repeated (step 406). If not the digital ADC output is between the lower and upper threshold values and the step is equal to or less than unity, in which case the procedure determines and outputs the following (step 420):

Run Time Electronic Gain $R_G = \text{GAIN}$

Scaling Factor $S_F = F_G/R_G$

Scaled output = ADC * $S_F$

Factory Gain (Calibration)

$F_G = \text{GAIN}$

We now describe a separate but related technique which can be applied after PCR amplification, using the same optical channel(s) and the same sample(s) for melt curve analysis to discover one or more peaks.

Figure 5:
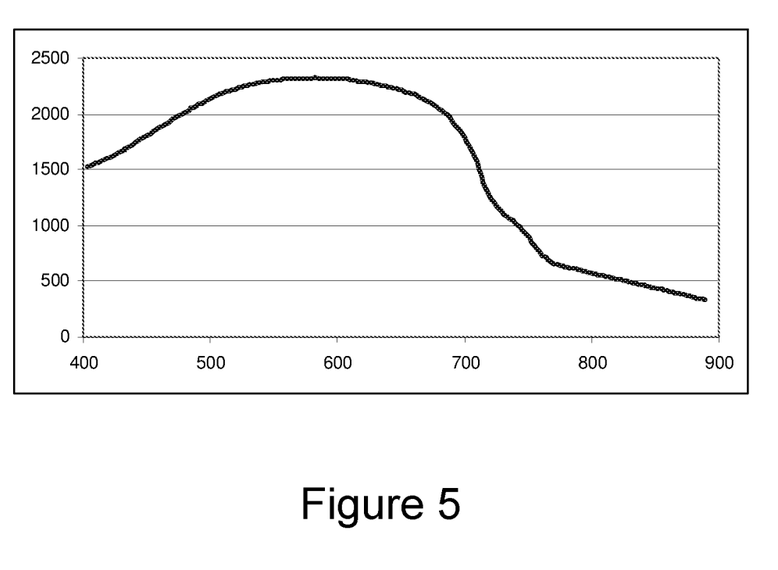
FIG. 5a shows an example of raw fluorescence data obtained by a linear temperature melt profile.

Thus referring to FIG. 5, this shows an example of a fluorescence waveform obtained by a linear temperature melt profile. This waveform is processed by means of the steps described below to obtain first order derivative (FOD) peaks that arise from changes in slope directions of this waveform.

Figure 6A:
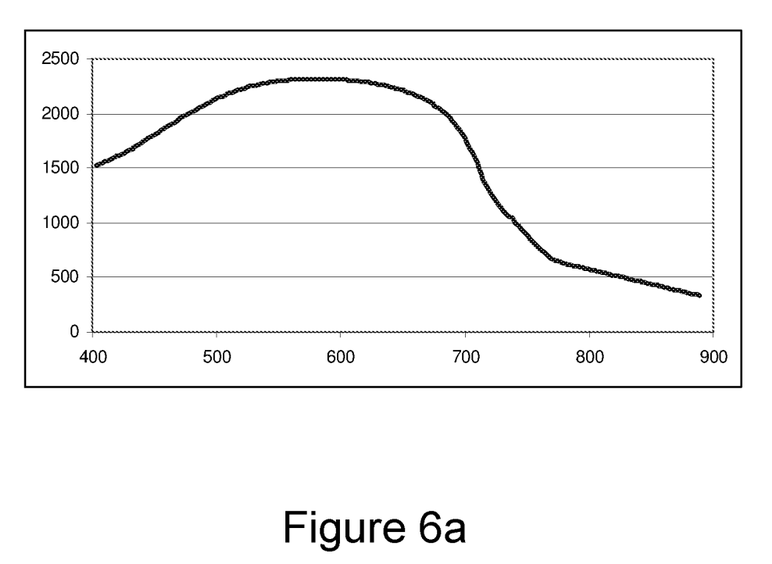
FIGS. 6a to 6j show stages in processing the waveform of FIG. 5 to identify one or more peaks according to an embodiment of the invention.

Thus, referring to FIG. 6a, this shows the output of an initial step of smoothing the raw fluorescence wave form over a window of 11 sample values, having extended/ extrapolated the data by a further 50 sample values, based on the average slope measured over the last 5 sample values of the actual recorded data. This artificially extended data is generated because the process of measuring the slope disposes of a segment of data at the end of the waveform.

Figure 6B:
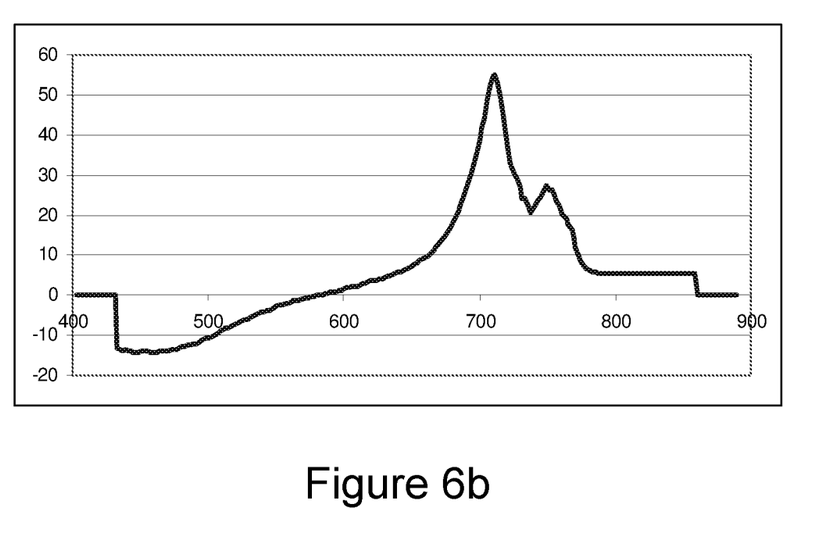

FIG. 6b shows the output of a process which obtains the slope of the waveform at each sample instant by using linear regression to obtain the best fit line through a set of 31 sample values balanced equally about the given sample point.

Figure 6C:
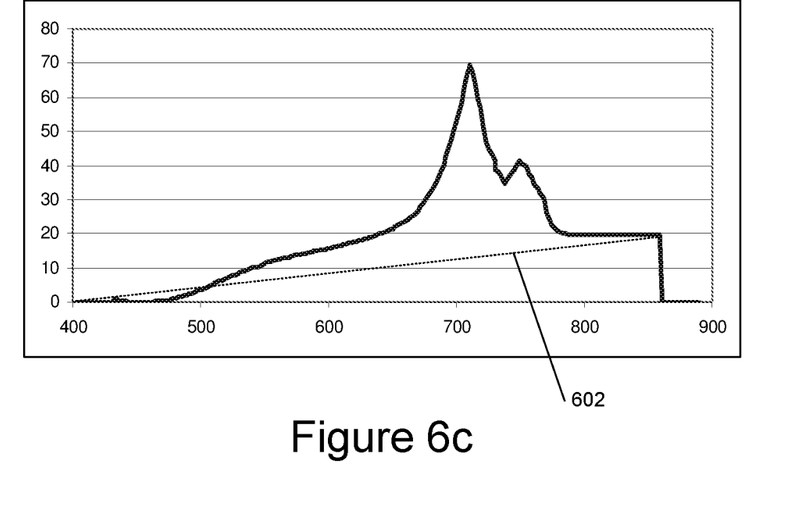

FIG. 6c shows the result of subtracting any offset so that the minimum value of this processed waveform lies on the zero axis.

Figure 6D:
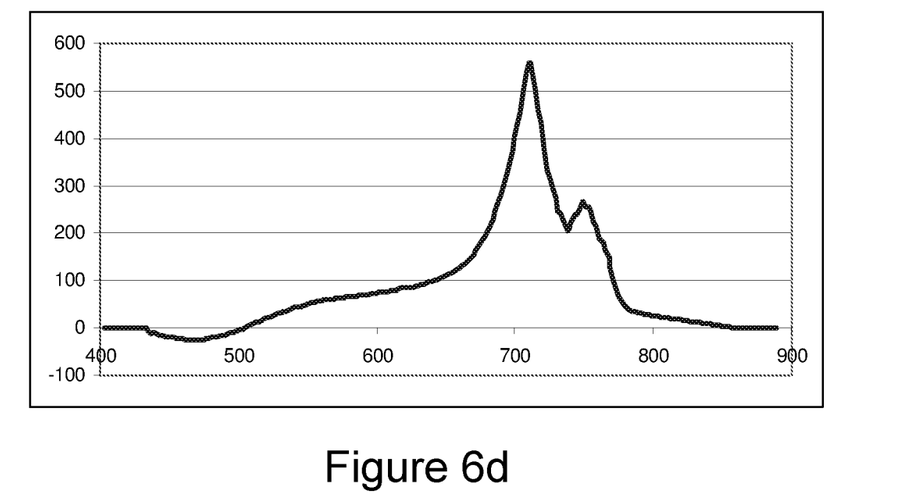
Figure 6E:
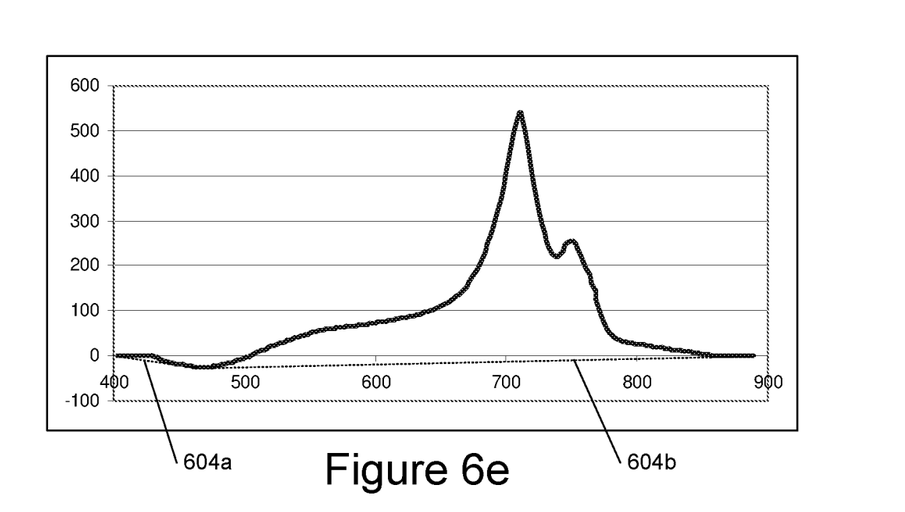

FIG. 6d shows the result of subtracting the straight line function that lies between the first value and last value (line 602 in FIG. 6c). FIG. 6e shows the output after smoothing this resulting waveform with a window of 11 sample values.

Figure 6F:
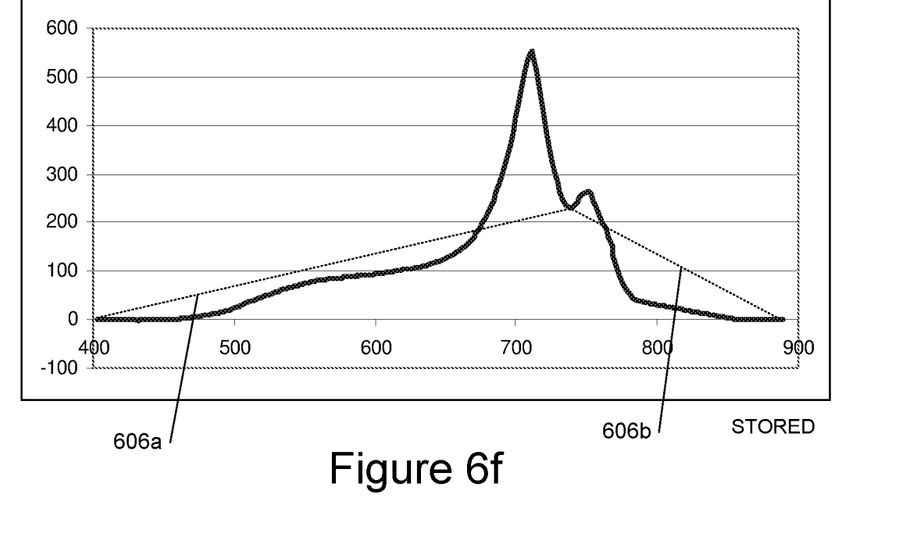

The procedure then subtracts a function defined by a straight line between each of the two end points and any negative minima (lines 604a, b in FIG. 6e), so that after this step the entire waveform should be positive. FIG. 6f shows the result of this process. This waveform is then stored for later use in determining which peaks are largest.

Figure 6G:
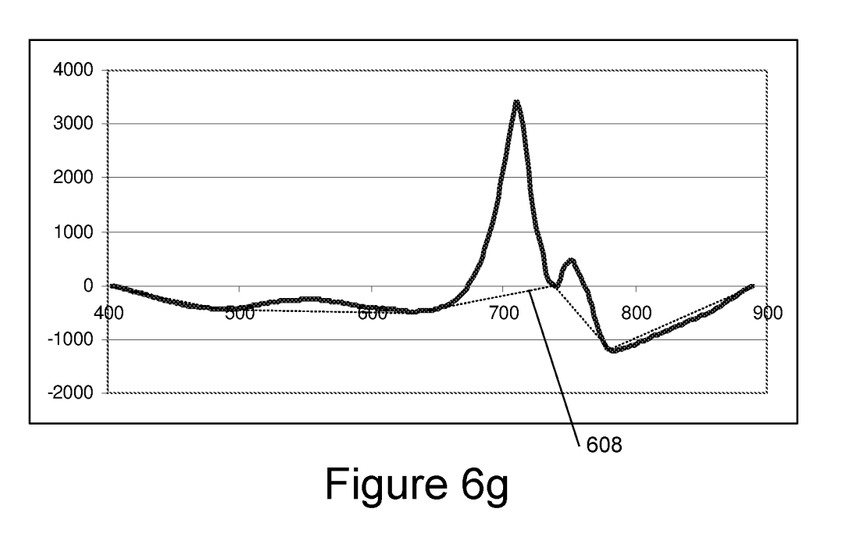

The procedure then identifies (all) the minima in the waveform of FIG. 6f and subtracts a straight line envelope that joins the minima values (lines 606a, b). This reduces the or each minimum to lie on the horizontal axis, as shown in FIG. 6g. This can result in introducing some additional, new minima below the zero axis, as illustrated in FIG. 6g. In preferred implementations, therefore, one or more additional passes are employed to address/resolve this, at least to a satisfactory degree. Thus in the illustrated example piecewise linear function 608 defines a further straight line envelope of the minima, which is subtracted to leave the waveform of FIG. 6h.

Figure 6H:
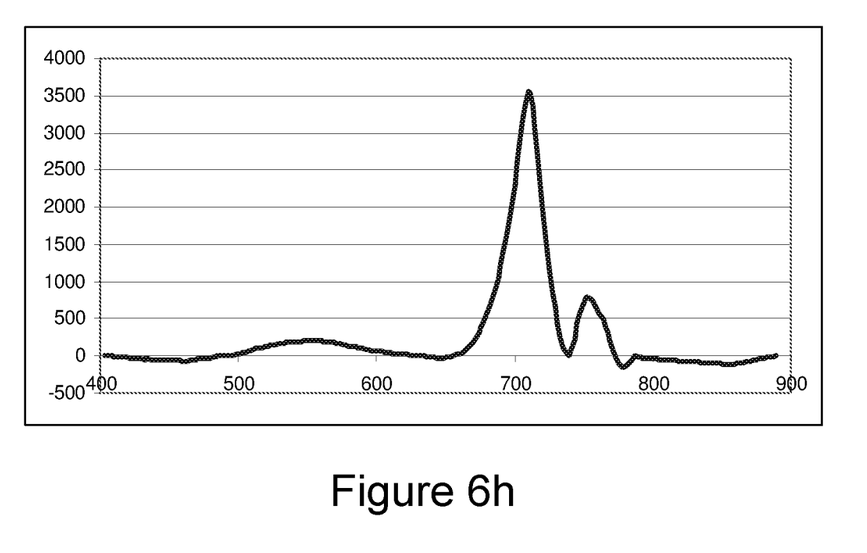
Figure 6I:
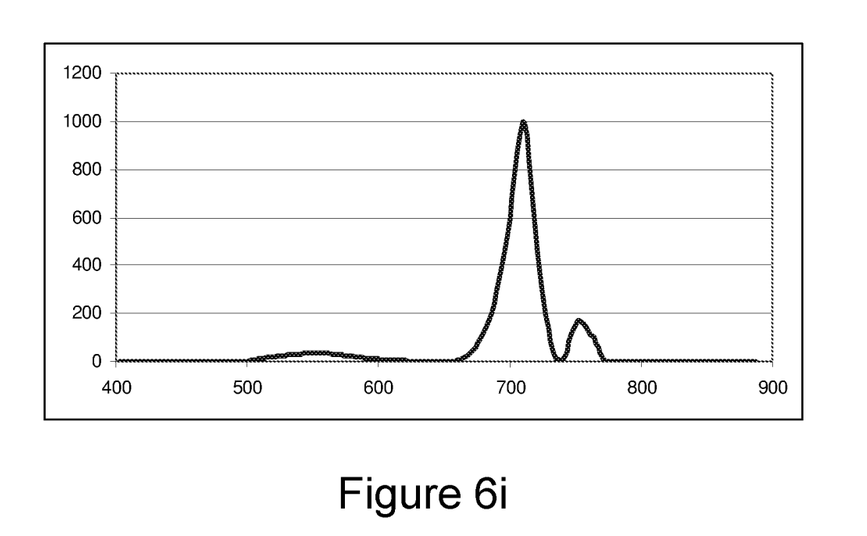

The procedure then identifies the largest peak in this waveform, using the waveform stored in the step illustrated by FIG. 6f, and identifies a scaling factor (non-linear power value) which when applied to the data of FIG. 6h scales this peak to a normalised value, in the illustrated example 1000—as shown in FIG. 6i.

Figure 6J:
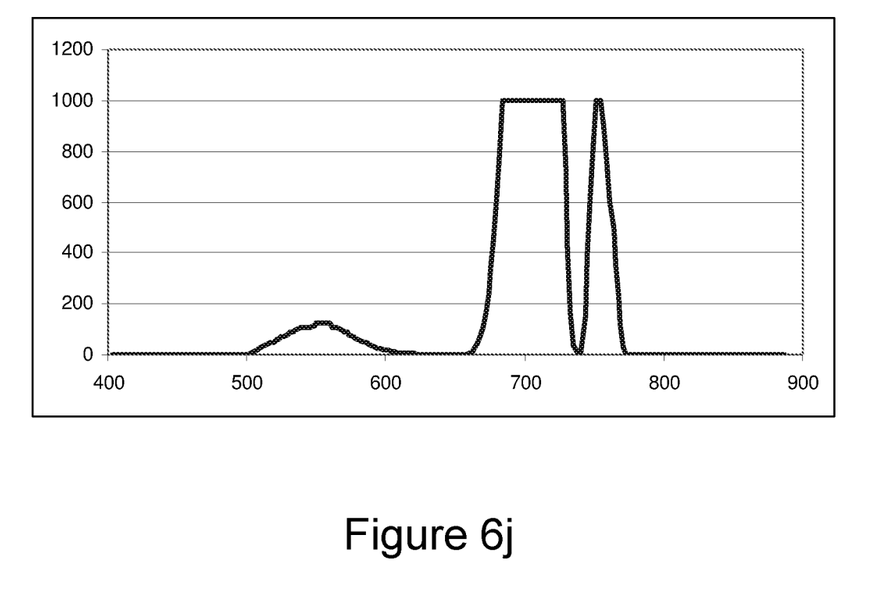

The procedure then determines the mean of this standardised waveform (FIG. 6i), and if this mean value is less than a threshold, for example 100, then the process of scaling to a normalised value and determining the average is repeated for the second largest peak, producing the waveform illustrated in FIG. 6j.

As each subsidiary peak is scaled, the overall mean of the waveform increases and thus by providing a threshold maximum for the mean value the number of subsidiary peaks which is identified by this procedure is limited: when the overall mean exceeds the threshold (100) this iterative/ recursive process is halted, and the resulting peaks are reported.

In some preferred implementations of the method the above described procedure is repeated from step (b), that is the slope determination which results in the output of FIG. 6b, but employing a narrower window of only 7 samples in the linear regression employed to measure the slope. The effect of this smaller window is to find many smaller peaks which would ordinarily result in a confusing number of false positives. However in preferred implementations all peaks in this second scan are rejected, except for any that lie within a predetermined or calculated distance of a peak that was found in the first scan. This predetermined/calculated distance may, for example, be a distance of 4 standard deviations (rejecting any peaks in the second scan that lie further than 4 standard deviations from a peak found in the first scan). This example threshold distance has been determined empirically and may be varied, for example according to the sample and/or experimental conditions and/or the balance between rejecting false positives and capturing small genuine signals.

Figure 7:
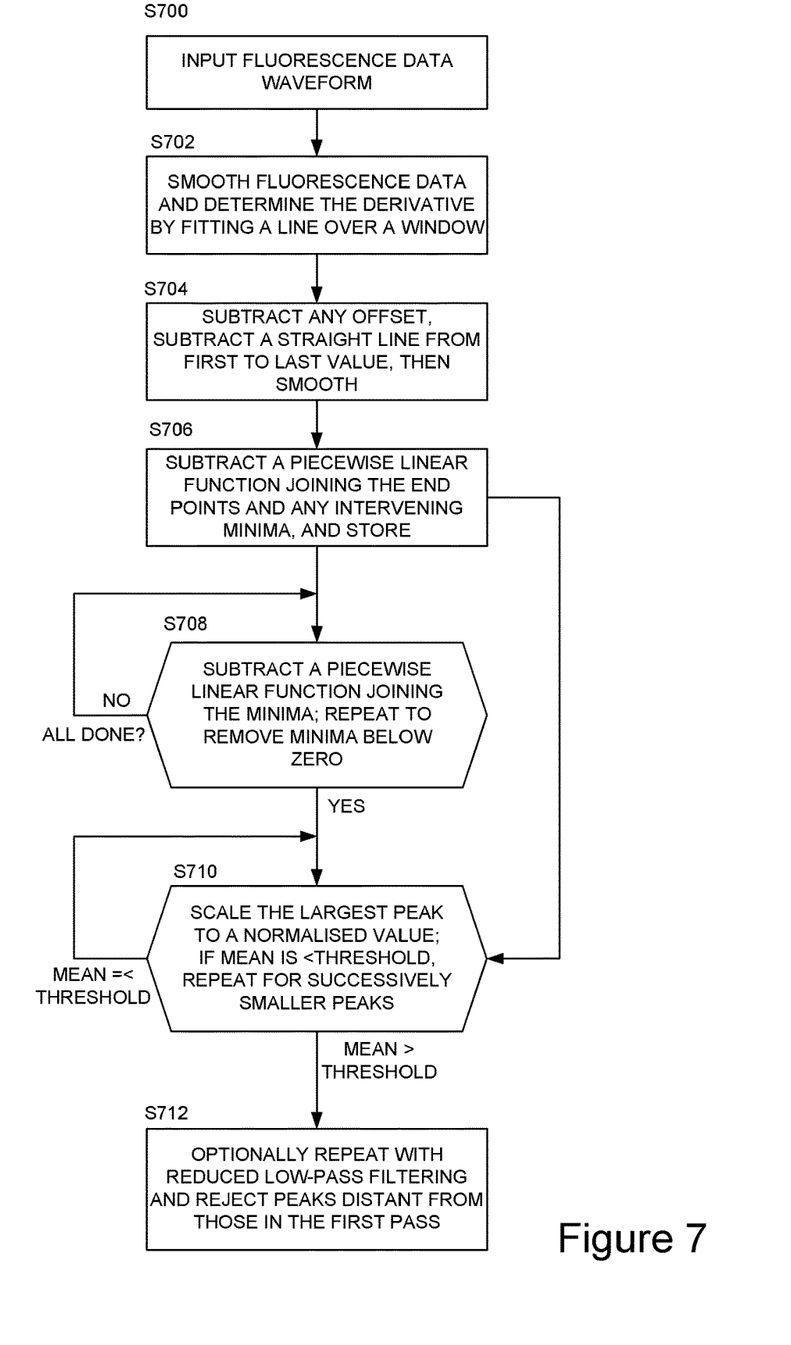
FIG. 7 shows a flow-diagram of a procedure to implement the processing illustrated in FIG. 6, for use in the instrument of FIG. 3.

FIG. 7 shows a flow diagram of a procedure to implement this end point analysis technique. Thus at step S700 the procedure inputs a fluorescence data waveform and then smoothes this data and determines the derivative with respect to temperature, preferably by fitting a line over a window (S702). The procedure then subtracts any offset, and then subtracts a straight line from the first to the last value, afterwards smoothing the result (S704), then subtracting a piecewise linear function joining the endpoints and any intervening minima, storing the result for later use (S706).

The procedure then subtracts a piecewise linear function joining the minima, optionally repeating this to remove one or more minima lying below a zero level, created by the subtraction process (S708). The process then scales the largest peak to a normalised value, and repeats this for successively smaller peaks until the mean is above a threshold (S710).

This identifies a set of one or more peaks in the melt (dissociation and/or association) curve fluorescence waveform and these may then be reported, for example by reporting the melt temperature(s) and/or peak heights and/or by providing a graphical output.

Optionally (step S712) the procedure is repeated with reduced low-pass filtering, to identify a larger number of subsidiary but potentially genuine peaks. These may then be filtered using the first set of larger peaks, for example to reject those which are too far distant from any peaks of the first set.

Applications for embodiments of the instruments and techniques we have described above include, but are not limited to: the detection of SNPs, the determination of allelic variation, the determination of DNA copy number, the analysis of material from bacterial and/or viral infections, for example for diagnostic purposes.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A quantitative PCR (qPCR) instrument for combined qPCR and dissociation and/or association curve analysis, the instrument having a plurality of optical channels, wherein each optical channel comprises:
   a fluorescence excitation source;
   a fluorescence detector having a signal output;
   an electronic analogue signal amplifier having an input coupled to said fluorescence detector signal output;

an analogue-to-digital converter (ADC) having analogue input coupled to an output of said analogue signal amplifier;
a quantified automatic gain control (AGC) loop wherein said AGC loop comprises a digitally controllable analogue electronic gain control circuit coupled between said signal output of said fluorescence detector and said analogue input of ADC, wherein said AGC loop is configured to apply a determined, numerical gain value to a fluorescence signal for said analogue input of said ADC;
the instrument further comprising:
a digital signal processing system configured to scale a digital output of said ADC responsive to said numerical gain value and to provide a digital fluorescence level signal from said scaled digital output; and
wherein said digital signal processing system is configured to control an electronic gain of said electronic analogue signal amplifier and to determine and store an initial calibration value of said electronic gain in non-volatile memory; and wherein said digital signal processing system is configured to determine digital scaling factors for said optical channels for scaling digital outputs of the ADCs of the channels to provide substantially the same digital fluorescence level signal output from each said channel for the same level of detected fluorescence, and to store in said non-volatile memory a combination of said digital scaling factors and initial calibration values of said electronic gain for said plurality of optical channels.

2. The qPCR instrument as claimed in claim 1 comprising a digital signal processing system coupled to said digital output of said ADC, and wherein said AGC loop comprises a digitally controllable analogue electronic gain control circuit coupled between said signal output of said fluorescence detector and said analogue input of ADC, and wherein said digital signal processing system is configured to determine said numerical gain value, to provide control data to said gain control circuit to apply said numerical gain value in the analogue signal domain, and to scale said digital output of said ADC by said numerical gain value to provide said digital fluorescence level signal.

3. The qPCR instrument as claimed in claim 2 wherein said digital signal processing system is configured to control an electronic gain of said electronic analogue signal amplifier and to determine and store an initial calibration value of said electronic gain in non-volatile memory.

4. The qPCR instrument as claimed in claim 3 wherein said digital signal processing system is configured to control said electronic gain of said electronic analogue signal amplifier to inhibit saturation of said ADC.

5. A method of operating a qPCR instrument having a plurality of optical channels, the instrument including:
a fluorescence excitation source;
a fluorescence detector having a signal output;
an electronic analogue signal amplifier having an input coupled to said fluorescence detector signal output; and
an analogue-to-digital converter (ADC) having analogue input coupled to an output of said analogue signal amplifier;
the method comprising:
calibrating said optical channel by adjusting an electronic gain of said electronic analogue signal amplifier;
storing a calibration value of said electronic gain in non-volatile memory;
applying automatic gain control (AGC) to an analogue electronic signal path of an optical channel during qPCR, wherein said AGC includes digitally determining a numerical gain value for said AGC;
determining a digital fluorescence level signal by scaling a digitized fluorescence signal from said optical channel by both said calibration value of said electronic gain and said determined numerical gain value for said AGC, wherein the method further comprises:
determining digital scaling factors for said optical channels for scaling digital outputs of the ADCs of the channels to provide substantially the same digital fluorescence level signal output from each said channel for the same level of detected fluorescence; and
storing in said non-volatile memory a combination of said digital scaling factors and initial calibration values of said electronic gain for said plurality of optical channels.

6. The method as claimed in claim 5 wherein said qPCR instrument is a multichannel qPCR instrument, the method further comprising calibrating each said optical channel such that substantially the same said digital fluorescence level signal is provided for each optical channel for substantially the same level of detected fluorescence.

7. The method as claimed in claim 5 further comprising using the same said instrument for performing a dissociation and/or association curve analysis on a result of said qPCR, continuing to apply said AGC after said qPCR during said dissociation and/or association curve analysis.

8. A quantitative PCR (qPCR) instrument for combined qPCR and dissociation and/or association curve analysis, the instrument having a plurality of optical channels, wherein each optical channel comprises:
a fluorescence excitation source;
a fluorescence detector having a signal output;
an electronic analogue signal amplifier having an input coupled to said fluorescence detector signal output;
an analogue-to-digital converter (ADC) having analogue input coupled to an output of said analogue signal amplifier; and
a quantified automatic gain control (AGC) loop configured to apply automatic gain control (AGC) to an analogue electronic signal path of said optical channel during qPCR, wherein said AGC includes digitally determining a numerical gain value for said AGC; and
wherein the instrument further comprises:
a digital signal processing system configured to:
calibrate said optical channel by adjusting an electronic gain of said electronic analogue signal amplifier;
determine and store a calibration value of said electronic gain in non-volatile memory;
determine a digital fluorescence level signal by scaling a digitized fluorescence signal from said optical channel by both said calibration value of said electronic gain and said determined numerical gain value for said AGC;
determine digital scaling factors for said optical channels for scaling digital outputs of the ADCs of the channels to provide substantially the same digital fluorescence level signal output from each said channel for the same level of detected fluorescence; and
store in said non-volatile memory a combination of said digital scaling factors and initial calibration values of said electronic gain for said plurality of optical channels.

9. The qPCR instrument as claimed in claim 1 further comprising:

a system to capture fluorescence data representing fluorescence (F) for a temperature (T) range including a double stranded DNA melting temperature;

an output to provide temperature data;

a processor, coupled to said input, to said output, to working memory and to program memory, said program memory storing instructions for controlling the processor to:

determine fluorescence derivative data representing a derivative (dF/dT) of said fluorescence with temperature;

identify a largest peak of said fluorescence derivative data;

scale said fluorescence derivative data such that said largest peak has a maximum at a defined value to provide scaled fluorescence derivative data;

determine a cumulative measure of said scaled fluorescence derivative data over said temperature range;

repeat said identifying, scaling and determining of said cumulative measure for successively small peaks of said fluorescence data until cumulative measure is greater than a threshold value; and output data representing temperatures of said identified peaks.

* * * * *